United States Patent [19]

Karas et al.

[11] Patent Number: 4,867,144
[45] Date of Patent: Sep. 19, 1989

[54] PLATE FOR CONNECTING BASE SPLINTERS WITH BONE SHAFTS

[75] Inventors: Wlodzimierz Karaś, Dabrowa Górnicza; Robert Granowski; Witold Ramotowski, both of Warsaw; Aleksander Tuziemski, Sosnowiec; Kazimierz Pilawski, Warsaw, all of Poland

[73] Assignee: Huta Baildon, Katowice, Poland

[21] Appl. No.: 38,053

[22] Filed: Apr. 14, 1987

[30] Foreign Application Priority Data

Apr. 14, 1986 [PL] Poland .................................. 258954

[51] Int. Cl.⁴ .............................................. A61F 5/04
[52] U.S. Cl. .......................... 128/92 Y F; 128/92 Y P
[58] Field of Search ................... 128/92 Y P, 92 Y F

[56] References Cited

U.S. PATENT DOCUMENTS

| 3,463,148 | 8/1969 | Treace | 128/92 Y P |
| 3,552,389 | 1/1971 | Allgower et al. | 128/92 Y P |
| 3,716,050 | 2/1973 | Johnston | 128/92 Y P |
| 4,408,601 | 10/1983 | Wenk | 128/92 Y P |
| 4,493,317 | 1/1985 | Klaue | 128/92 Y P |
| 4,506,662 | 3/1985 | Anapliotis | 128/92 Y F |
| 4,524,765 | 6/1985 | de Zbikowski | 128/92 Y P |

FOREIGN PATENT DOCUMENTS

| 451868 | 10/1948 | Canada | 128/92 Y P |
| 2233973 | 1/1975 | France | 128/92 Y P |
| 2405706 | 5/1979 | France | 128/92 Y P |

Primary Examiner—John D. Yasko
Attorney, Agent, or Firm—Ladas & Parry

[57] ABSTRACT

This invention relates to a plate for connecting bone splinters with bone shafts. The plate has a "T"-shape with a short transverse arm (1) and a longitudinal leg (2) situated perpendicularly to each other. In the transverse arm (1) and longitudinal leg (2) there are sets of pressure holes (3) each having on one side of the plate a conical shape and on the other side an oval shape with a major axis extending in the identical direction as that of the axis (0) of the longitudinal leg (2). Along the same axis, in which each oval tapered pressure hole (3) is situated, in said other side of the transverse arm (1), there are elongated grooves (4). In said other side of the longitudinal leg (2) of the plate, along its longitudinal axis (0), there also runs a groove (6).

1 Claim, 2 Drawing Sheets

PLATE FOR CONNECTING BASE SPLINTERS WITH BONE SHAFTS

CROSS REFERENCE TO RELATED APPLICATIONS

Karas et al, U.S. Ser. No. 07/033,410 filed Apr. 1, 1987 is entitled "Drill Setting Guide for Drilling Holes in Bones".

Karas et al, U.S. Ser. No. 07/132,937 filed Dec. 15, 1987 is entitled "Stabilizer for the Treatment of the Fracture of the Neck and Upper Metaphysis of the Femur", and discloses a special bolt nut configuration and an associated bone bolt having a threaded shank to which the nut is applied.

Karas et al, U.S. Ser. No. 07/133,059 is entitled "Bone Bolt Nut Wrench" and discloses a tool specially adapted for application of a threaded bone screw or bone bolt and an associated bolt nut such that the single tool can be used to apply a bone screw or bolt as well as to apply and remove a threaded bone bolt nut.

BACKGROUND OF THE INVENTION

This invention relates to a plate for connecting bone fragments, in particular base splinters with bone shafts.

Nowadays, in orthopedic surgery there is a tendency to ensue, apart from connection of bone spinters, a firm internal stabilization thereof and to eliminate, in this way, a stiff dressing. This is a therapeutic method called stable osteosynthesis. One of variants of this therapy is connection of bone splinters by means of plates with holes and bone screws.

Those skilled in this field of art are aware of means providing for a compressive connection of bones consisting of a thrust plate screwed onto the bone by means of or screws with a cortex thread, with a head in the form of a shoulder, or a shaped screw nut, which is associated with a necessary operative cut indispensable for a positioning of the fracture. In the case of some fracture of humerus, elbow osteosynthesis of humerus, fracture of upper tibia and some other lesions in the vicinity of the connection, special T shaped plates are used. A common feature of the known plates is a widened fixing part which has two, or more round hole, Hole axes are either parallel, or inclined at certain angle to one another. The fixing part is provided with several round holes, or a combination of round and oval holes.

During the first stage of the operation the fixing arms of the plate are fixed by means of screws to the bone splinters. Next, the shaft portion of the plate is fastened to the bone. If necessary, before fixing the shaft portion, the bone splinters are pressed axially to each other by means of a clamping device, or an automatic compression is used.

The design of the plate and screws so far used has not made possible stiffening of the fracture in the form of a stabilizer. In order to obtain a good stabilization of the spinters one must press the plate with a considerable force against the bone by means of screws. Such a pressure of the plate against the bone, together with isolation of a large bone area by the plate from the surrounding tissues either worsens, or completely precludes revascularization of the cortex layer lying under the plate. This has been confirmed by numerous histopathologic examinations of bone splinters taken from under the plate during removal of connecting material.

SUMMARY OF THE INVENTION

In order to avoid a lesion of the bone fracture being treated, or in order to avoid any distubances making impossible the correct course of treatment, the plate of a new design has been developed.

A prefered embodiment of the invention comprises a T-shaped plate having oval tapered pressure holes situated in the shorter traverse arm, whose directions are identical as the direction of the longitudinal axis of the longer shaft arm. In the same axis in which each oval tapered pressure hole is situated, in the bottom part of the shorter there is a groove.

The plate according to the invention is used with bone screws with cortex thread on one side and metric thread on the other side. The plate is superimposed on the screws which have been previously screwed into the bone splinters and secured thereto with nuts threaded on the side of the metric thread resulting in a structure having the features of a clamp stabilizer. The plate makes possible the connection of fractures of anatomical neck of humerus, elbow bases of humerus, upper tibia bases, as well as other lesions in the neighbourhood of base. Owing to its design, and application of a double thread separated from each other by suitable shoulder, the plate may be used either under skin, or above skin. Elevation of the plate above the bone eliminates its pressure against the bone and isolation by the plate of a large area of the bone from the surrounding tissues which prevents revascularization of the cortex layer situated under the plate.

BRIEF DESCRIPTION OF THE DRAWINGS

An embodiment is shown in the accompanying drawing, wherein.

DESCRIPTION OF PREFERRED EMBODIMENT

Figure 2:
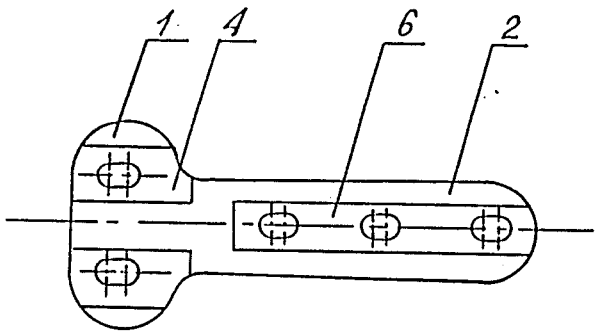
FIG. 2 shows the bottom view of the plate.
Figure 1:
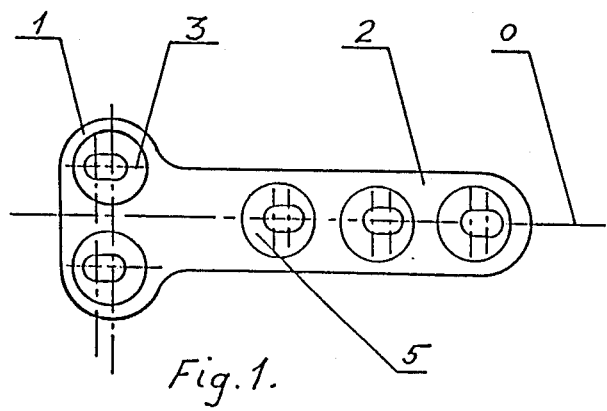
FIG. 1 presents the top view of the plate.
Figure 3:
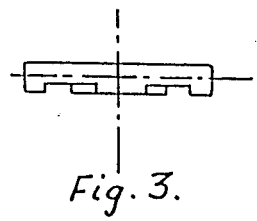
FIG. 3 shows the side view of the plate when viewed upon from the side of the base part.
Figure 5:
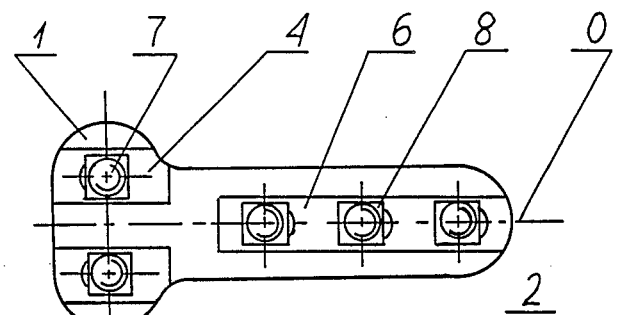
FIG. 4 and FIG. 5 show, respectively the bottom view of the plate, together with screws.
Figure 6:
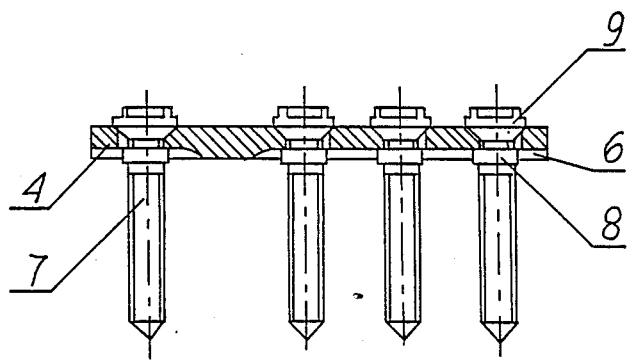
FIG. 6 shows the longitudinal section of the plate, together with screws.
Figure 7:
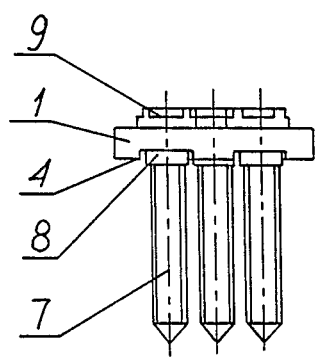
FIG. 7 shows the side view of the plate viewed upon from the side of the base part, together with screws.
Figure 4:
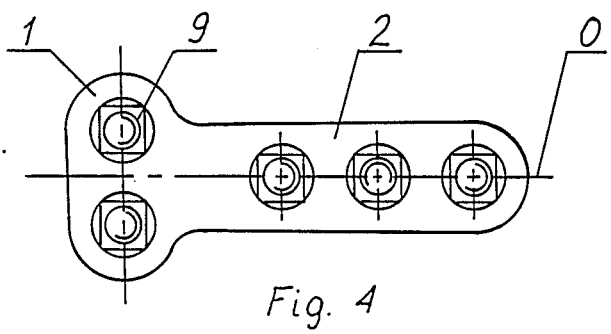

Referring to FIG. 1, a T-shaped plate has a shorter base arm 1 and a longer shaft arm 2 situated perpendicularly to each other. In the base arm 1 there are two oval tapered pressure holes 3 of the same direction as the longitudinal axis O of the longer arm shaft 2. Referring to FIG. 2, in the bottom portion of the base arm 1 there are grooves 4, lying in the same axis, where all oval tapered pressure holes 3 are situated. In the longer shaft arm 2 in the longitudinal axis O there are oval tapered pressure holes 5. In the bottom portion of the shaft arm 5 in its longitudinal axis O there runs a groove 6.

The plate is to be mounted on a fractured bone base and bone shaft in the following way. At first, screws 7 with a cortex thread are to be screwed into the holes drilled in the broken bone fragments so that shoulder 8 is not in contact with the bone. Next, on the screws 7 thus screwed, a plate is to be introduced so that the shorter base arm 1 rests on the screws 7, introduced in the base part of the bone, and the longer shaft arm 2 rests on the screws 7, introduced into the bone shaft. Shoulders 8 of screws 7 enter the grooves 4 and 6. On the portions of the screws 7 with metric thread protruding above the oval tapered holes 3 and 5 suitable nuts 9 should be screwed down. Tightening of nuts 9 is accompanied by a displacement of the screw 7 with oval tapered hole 3 and 5. When the screws 7 are being shifted the fracture fissure is being closed and pressed.

We claim:

1. A "T" shaped plate for connecting base fragments with bone shafts, comprising a shorter transverse arm for mounting on a bone fragment and an elongated arm for mounting on a bone shaft, said elongated arm having a longitudinal axis, and compression holes disposed in said arms, characterized in that each hole in the shorter transverse arm, on one side of the plate surface opposite to the bone fragment has a tapered shape around its entire circumference, with a circular rim, and on the other side of the plate intended to be elevated above the bone, each hole has an oval shape with a longer main axis and a shorter transverse axis, wherein the longer main axis of the oval shape of each hole in the shorter transverse arm is parallel with said longitudinal axis of the elongated arm, said transverse arm having an elongated groove below each opening formed in the bone-facing surface of the plate, said groove being located so that its longitudinal axis lies in the same main axis of the oval shape of each opening in the transverse arm, and each groove is perpendicular to the shorter transverse arm, each groove having its lateral surfaces perpendicular to each other, the width of each groove being at least equal to the length of the shorter transverse axis of the oval shape of each hole, and the depth of each groove is smaller than its width.

* * * * *